United States Patent
Mayernik et al.

(10) Patent No.: US 7,627,487 B2
(45) Date of Patent: Dec. 1, 2009

(54) COMPREHENSIVE HEALTHCARE WASTE ASSESSMENT SYSTEM

(75) Inventors: Geoffrey D. Mayernik, Cincinnati, OH (US); Jeff D. Crawford, Cincinnati, OH (US)

(73) Assignee: Healthcare Waste Solutions, LLC, Cincinnati, OH (US)

( * ) Notice: Subject to any disclaimer, the term of this patent is extended or adjusted under 35 U.S.C. 154(b) by 196 days.

(21) Appl. No.: 11/624,022

(22) Filed: Jan. 17, 2007

(65) Prior Publication Data

US 2008/0059383 A1 Mar. 6, 2008

Related U.S. Application Data

(60) Provisional application No. 60/759,363, filed on Jan. 17, 2006.

(51) Int. Cl.
*G06Q 10/00* (2006.01)
*G06Q 30/00* (2006.01)
*G06F 17/00* (2006.01)
*G06G 7/00* (2006.01)

(52) U.S. Cl. .......................................... 705/1; 705/400

(58) Field of Classification Search .................... 705/1, 705/400
See application file for complete search history.

(56) References Cited

U.S. PATENT DOCUMENTS

| 5,347,274 | A | 9/1994 | Hassett |
| 6,256,640 | B1 | 7/2001 | Smalley et al. |
| 6,490,569 | B1 | 12/2002 | Grune et al. |
| 6,725,446 | B1 | 4/2004 | Hahn et al. |
| 2002/0147502 | A1 * | 10/2002 | Price et al. ..................... 700/1 |
| 2003/0204420 | A1 | 10/2003 | Wilkes et al. |
| 2004/0267595 | A1 | 12/2004 | Woodings et al. |
| 2005/0273361 | A1 | 12/2005 | Busch |

OTHER PUBLICATIONS

Elaine Hiruo, "Utility Fees Adequate to Cover Nuclear Waste Program, DOE Says." Jul. 2, 1987 Nucleonics Week, vol. 28, No. 27, p. 2.*

* cited by examiner

*Primary Examiner*—John W Hayes
*Assistant Examiner*—Allen J Jung
(74) *Attorney, Agent, or Firm*—Wood, Herron & Evans, LLP

(57) ABSTRACT

A computer implemented method, apparatus and program product analyzes medical waste processes by determining waste cost information for a number of waste streams. The waste cost pricing information is organized, formatted, associated or otherwise processed for presentation in a manner that facilitates waste cost analysis.

17 Claims, 5 Drawing Sheets

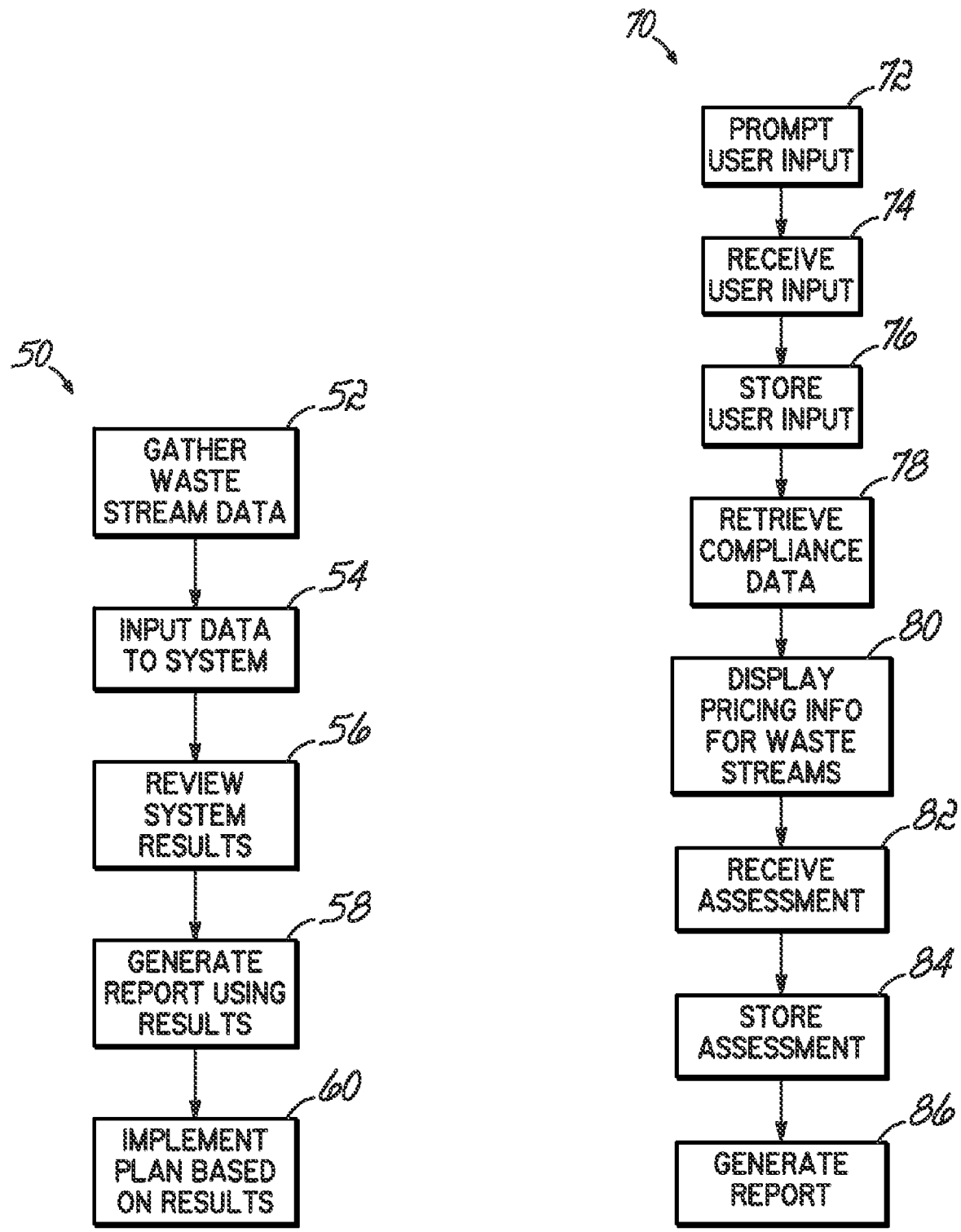

Figure 5:
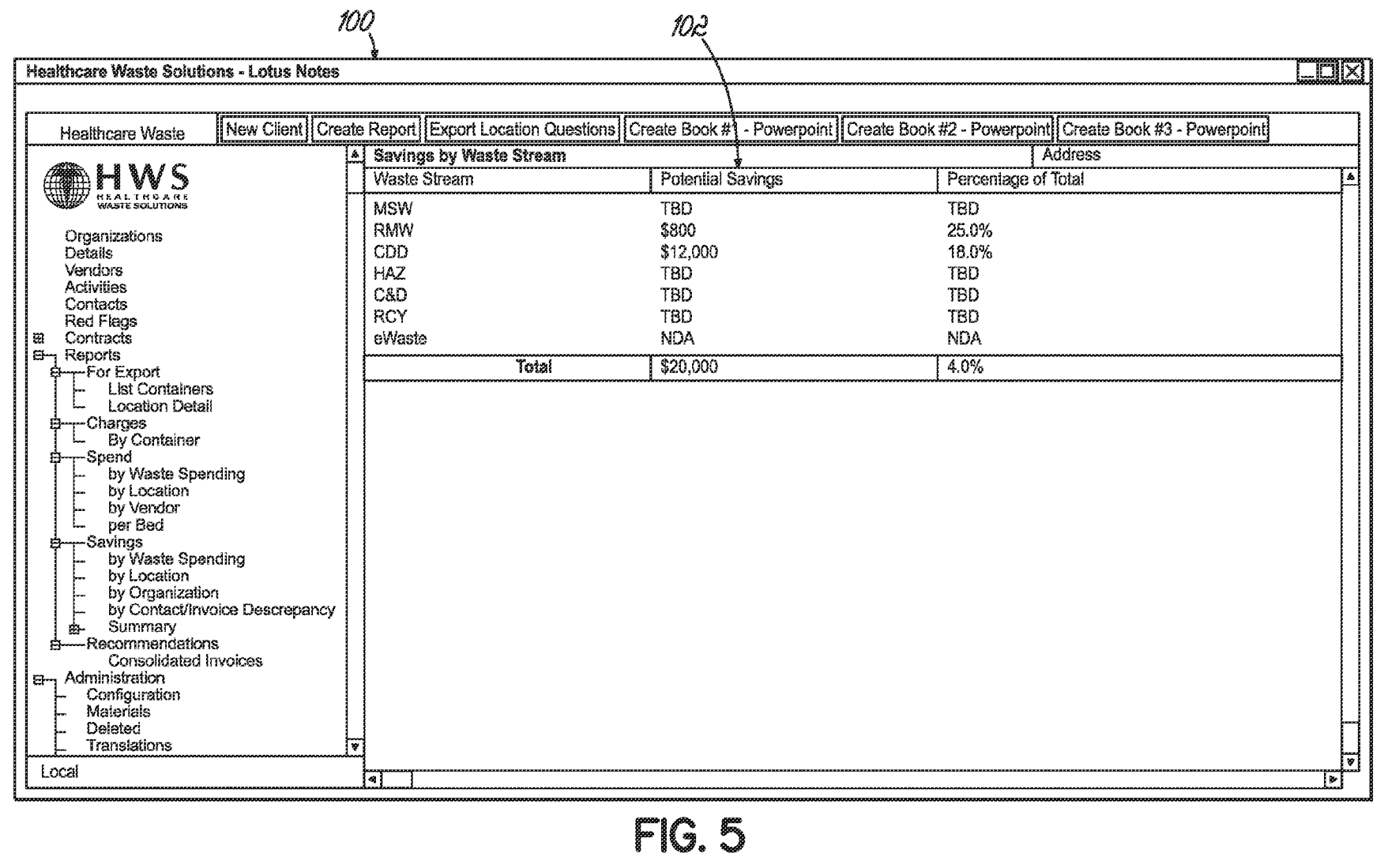

| Waste Stream | Potential Savings | Percentage of Total |
|---|---|---|
| MSW | TBD | TBD |
| RMW | $800 | 25.0% |
| CDD | $12,000 | 18.0% |
| HAZ | TBD | TBD |
| C&D | TBD | TBD |
| RCY | TBD | TBD |
| eWaste | NDA | NDA |
| Total | $20,000 | 4.0% |

FIG. 6

Healthcare Waste Solutions - Lotus Notes

| New Client | Create Report | Export Location Questions | Create Book #1 - Powerpoint | Create Book #2 - Powerpoint | Create Book #3 - Powerpoint |

Healthcare Waste
- Organizations
- Details
- Vendors
- Activities
- Contacts
- Red Flags
- Contracts
- Reports
  - For Export
    - List Containers
    - Location Detail
  - Charges
    - By Container
  - Spend
    - by Waste Spending
    - by Location
    - by Vendor
    - per Bed
  - Savings
    - by Waste Spending
    - by Location
    - by Organization
    - by Contact/Invoice Descrepancy
    - Summary
  - Recommendations
    - Consolidated Invoices
- Administration
  - Configuration
  - Materials
  - Deleted
  - Translations

110 →

Savings by Waste Stream

| Waste Stream | Actual Savings | Percentage of Total | Address |
|---|---|---|---|
| MSW | $4,000 | 2.0% | |
| RMW | $7,500 | 5.0% | |
| CDD | $12,000 | 12.0% | |
| HAZ | $6,000 | 3.0% | |
| C&D | $2,000 | 3.0% | |
| RCY | $3,000 | 2.0% | |
| eWaste | $8,500 | 9.0% | |
| Total | $41,000 | 7.0% | |

112

COMPREHENSIVE HEALTHCARE WASTE ASSESSMENT SYSTEM

CROSS REFERENCE TO RELATED APPLICATIONS

This application claims benefit of priority to Provisional Patent Application No. 60/759,363, entitled "Healthcare Waste Assessment Tool," filed on Jan. 17, 2006 by Geoffrey Mayernik, which application is incorporated herein by reference in its entirety.

FIELD OF THE INVENTION

The present invention generally relates to health care services, and more particularly, to facilitating the disposal of healthcare related waste.

BACKGROUND OF THE INVENTION

Healthcare facilities around the world allocate huge portions of their budgets to managing waste. Hospital waste is unique in several ways. For instance, there is a large variety of different types of waste, or waste streams, having very different handling and other disposal requirements. Healthcare waste streams are generally categorized to include solid, regulated medical and recycling waste. Other waste streams include confidential document, hazardous, and construction debris waste.

For instance, hospitals employ toxic chemicals and hazardous materials for numerous diagnostic and treatment purposes. Examples of hazardous materials include formaldehyde, photographic chemicals, radio nuclides, solvents, mercury, waste, anesthetic gases and other toxic, corrosive chemicals.

Solid, regulated medical waste generally includes materials generated in the diagnosis, treatment, research, or immunization of human beings or animals. Examples of regulated medical waste includes: cultures and stocks, pathological wastes, human blood and blood products, sharps, certain animal waste and isolation wastes. Other types of solid (unregulated and nonhazardous) waste is referred to within the industry as the solid waste stream.

Confidential material produced by healthcare facilities comes in many forms. From patient records to billing reports to pharmacy bottles, wristbands, and a variety of other printed materials, private patient information abounds within the healthcare system. Controlling and limiting the hospital's risk in unintentional disclosure of this information is challenging.

Hospitals and other healthcare service providers additionally must manage tons of recycling waste, in addition to periodic construction debris attributable to expansion or remodeling.

Despite of the enormous dollars spent on managing waste, few healthcare systems have historically focused on maximizing the value received in this area. With continued pressure on healthcare providers to be efficient and cost effective, however, many hospitals and other providers recognize the need to accurately assess and streamline their waste stream disposal operations.

Such waste stream assessments are complicated by a number of factors, however. One obstacle to an accurate accounting of waste disposal stems from the varying processes by which different types of waste streams are traditionally disposed. Conventional in-house assessments and consultations generally focus on one, individual waste stream. This singular focus is largely because each waste stream may have vastly different disposal requirements from other streams. Most experts in the field specialize in a particular waste stream. Even within the healthcare field, few personnel have the technical know how or resources to evaluate the discrepant processes and requirements of different waste streams. Other challenges relate to different state and federal disposal regulations. Such codes vary not only per different waste streams, but also according to locality.

For example, each waste stream's economic structure is unique to that particular waste stream. The unique structure takes into account specific charges known for each stream. For instance, haul rates and per ton pricing for solid waste, pricing for confidential documents, per pound/per contained charges for regular medical waste, and other charges may vary per specific waste stream application.

Another challenge facing healthcare facility managers includes the volumes of invoices and paperwork associated with each, individual stream of waste. Many facility managers struggle to maintain the volumes of paperwork in any practically usable state.

As a result, many facility managers are relegated to working with dozens of vendors and having to process thousands of different invoices. The billed rates may in some instances be inconsistent with the contracted rates, and those invoices may include numerous unexpected charges and fees. Even where administrators attempt to diligently track invoices, they are rarely aware of discrepancies between contracts and invoices due to the sheer volume of paperwork and contractors.

Tracking hazardous waste in hospitals is often further complicated by a lack of available records of waste generation. For example, facility managers may lack maintenance paperwork indicative of the status of existing equipment. Review of such records is nonetheless required for service issues, such as sharps containers that are worn out, or not properly cleaned, sized or positioned. Lack of comprehensive and meaningful records may further lead to hazardous waste being mixed with infectious waste, as well as to the disposal of potentially hazardous wastes into the sewer.

In one sense, the absence of a comprehensive, "big picture" perspective of waste management can lead to inaccurate, inconsistent and unmeaningful waste stream assessments. Conventional accounting practices provide little incentive for providers to be more efficient, and provide limited information and options that could lead to improvement. As a consequence, healthcare providers may be reluctant to spend funds on assessments that could otherwise potentially identify economic waste arising from mistake and inefficiency.

There consequently exists a need for an improved manner of assessing medical waste processes.

SUMMARY OF THE INVENTION

The present invention provides an improved computer implemented method, apparatus and program product for assessing medical waste processes. Aspects of the invention include receiving user input to obtain requested pricing information for products or services associated with a plurality of waste streams. The requested pricing information may be retrieved by accessing a database storing pricing information associated with a plurality of waste products and waste services associated with the plurality of waste streams. The requested pricing information may be output to the user.

Aspects of the invention include automatically generating a report including the pricing information. An exemplary report may include, for instance, a listing of multiple containers being used at a facility. The report may further include a waste recommendation to improve the medical waste process. One such waste recommendation may include generating an invoice accounting for at least two of the plurality of waste streams. The report of another or the same embodiment may include a time line for implementing a waste recommendation. The pricing information may comprise compliance data pertinent to the waste streams, among other financial and regulatory information. The pricing information may be used to determine a waste opportunity and recommendation. Where desired, the recommendation may include projected savings as compared to current waste management practices. After implementation of the waste solution, other reports may highlight the benefits of implemented waste solutions by comparing actual, achieved savings to costs incurred prior to the implementation.

Embodiments may provide synergistic benefits by, in part, leveraging and realizing efficiencies across multiple waste streams. Such benefits typically include lower aggregate costs, and more efficient billing and waste removal. Other benefits may include improving operating practices, eliminating or reducing use of carcinogenic chemicals, and increased use of analytical instrumentation. Aspects of the invention may improve inventory control utilization by using improved computer tracking and inventory methods, as well as the elimination of oil-based paints and maintenance. Other benefits may relate to recycling and reclamation recommendations.

These and other advantages and features, which characterize the invention, are set forth in the claims annexed hereto and forming a further part hereof. However, for a better understanding of the invention, and of the advantages and objectives attained through its use, reference should be made to the Drawings, and to the accompanying descriptive matter, in which there is described exemplary embodiments of the invention.

BRIEF DESCRIPTION OF THE DRAWINGS

FIG. 2 is a flowchart having steps for conducting a comprehensive assessment of multiple waste streams using the system of FIG. 1 to input and analyze waste stream information towards determining pertinent pricing information and implementing a comprehensive plan.

FIG. 3 is a flowchart having process steps executable by the system of FIG. 1 for assessing and outputting pricing information pertinent to multiple waste streams for the healthcare facility.

FIG. 4 shows an exemplary computer screen displayed by the system of FIG. 1 and configured to prompt input from the user regarding current waste stream practices, as outlined in the text describing FIG. 3.

FIG. 5 shows an exemplary report generated by the system of FIG. 1 and configured to communicate multi-waste stream pricing information to a user, as also outlined in the text describing FIG. 3.

FIG. 6 shows an exemplary report generated by the system of FIG. 1 and configured to communicate realized, actual benefits of an implemented waste solution.

DETAILED DESCRIPTION

Figure 1:
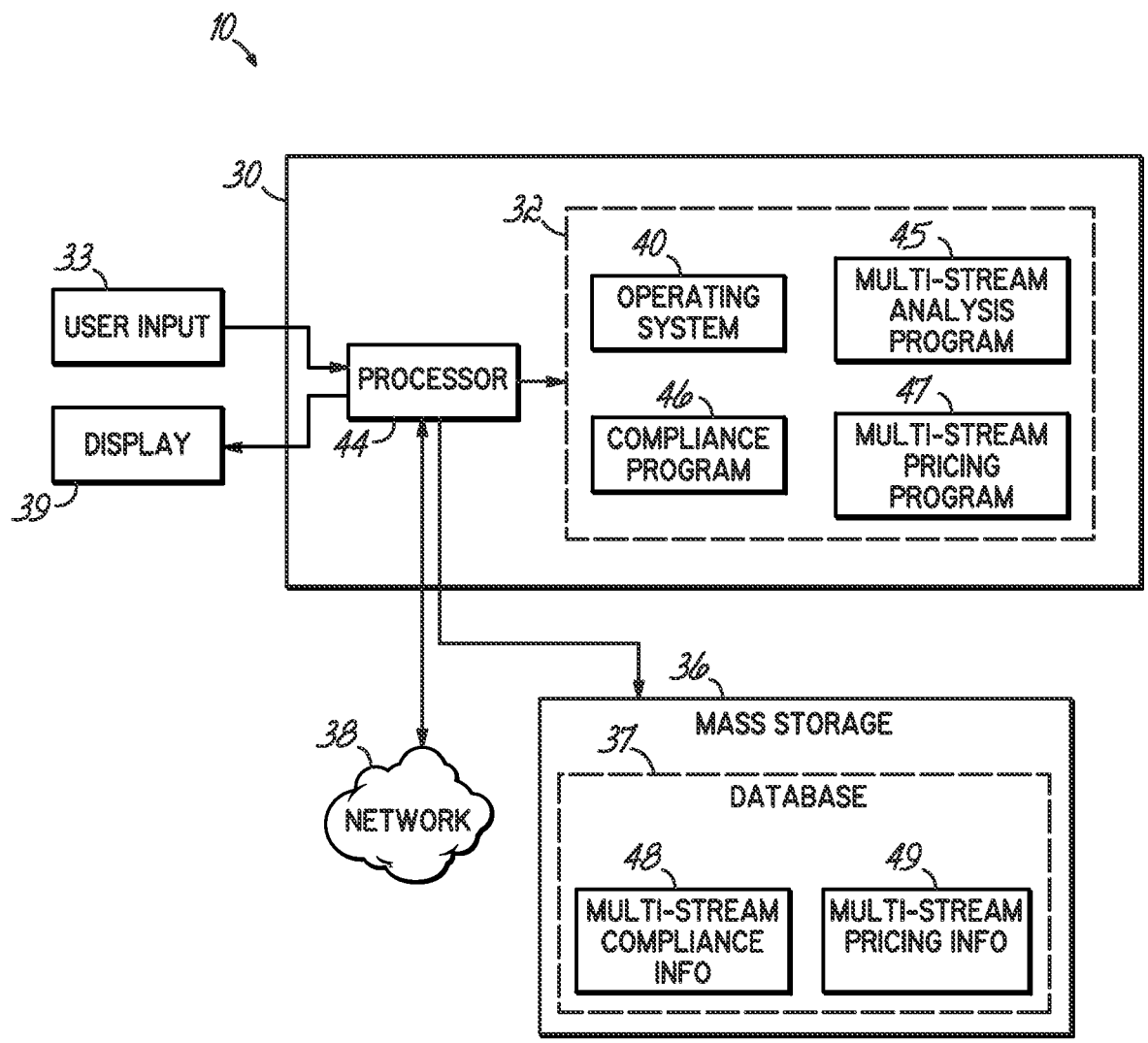
FIG. 1 is a block diagram of a networked computer system configured to facilitate a comprehensive analysis of multiple waste streams for a healthcare facility.

A computer implemented method, apparatus and program product analyze medical waste processes by determining waste cost information for a number of waste streams. The waste cost pricing information is organized, formatted, associated or otherwise processed for presentation in a manner that facilitates waste cost analysis.

Embodiments consistent with the invention provide comprehensive economic, worker safety and environmental compliance analysis of a health organization's waste operation. In one sense, aspects of the invention present a complete solution for healthcare waste steams. The solution typically accounts for all solid waste streams generated by a healthcare facility, including, among others, solid waste, medical waste, hazardous waste, recycling, electronic waste, confidential document destruction, and construction debris. Embodiments may further provide savings opportunities based on right-sizing and component pricing. Compliance with federal OSHA standards and other federal and state codes may also be automatically facilitated.

Embodiments consistent with the invention facilitate onsite review developed and prompted by a computer assessment program. The program typically includes detailed and focused questions, as well as other data entry prompts for each department of a healthcare organization. Apparatuses and processes consistent with the invention may be used in this onsite capacity to gather information regarding current waste disposal procedures. Such procedures are typically stored and categorized within a database utilized by the programmatic processes.

Aspects of the invention thus facilitate the automated identification, processing and storage of suspected and known sources of waste. Entry for hazardous waste, for example, may include laboratories, pathology, pharmacies, radiology, surgery, dialysis, embalming, nursing units, nuclear medicine, mercury from broken equipment, red bag (infectious wastes), and storage areas for raw material and waste. In one example, hazardous wastes generated by the radiology/imaging department may include fixer, developer and mercury. A central sterile supply department of a hospital may generate ethylene oxide. A pharmacy may generate antineoplastic wastes, which must be hauled off site for incineration.

Assessments of a healthcare system typically include the review and programmatic processing of applicable invoices and contracts. Contract terms, rate structures, rental agreements and invoice practices may be examined, validated and stored in a searchable format. In this manner, information is input into the database for use in determining the total cost for each waste stream.

More specifically, embodiments consistent with the invention facilitate assessments that include a full examination of all waste streams generated by one or more facilities. Data entry from the individual waste streams may be prompted, received and analyzed from their points of generation and collection, through the facility to the staging and storage areas where services are received. This analysis may include examining the methods for transporting the various waste streams through the facility, as well as the number of personnel dedicated to handling the waste. Other data may regard a waste run schedule for all containers, as well as information indicative of all shifts for all locations and service points.

Data relating to facility equipment may also be entered and analyzed. Such equipment may include compactors, bailors, shredders, on-site treatment equipment and other capital equipment related to waste handling. Loading docks and storage areas may likewise be examined, and data indicative of current waste handling equipment and service levels may be entered. Embodiments of the program may initiate and direct users to conduct interviews with key facility personnel.

Embodiments of the computer based assessment tool may thus ensure that all required information is collected in a consistent manner and is available for analysis each day to one or more networked or standalone users. Features of the assessment tool include rapid and accurate collection, flexible information storage, multi-team use and access, easy reporting to answer questions and fact based analysis. This feature allows skilled personnel to focus on results and leverage past experience.

Embodiments consistent with the invention thus facilitate a best practice database, analysis techniques and history to provide high value results. Reporting provides key information on focus areas where problems may exist. Cost analysis and savings summaries provide real cost benefit projections.

The computer implemented analysis typically produces a detailed economic report that lists each waste container being serviced at a facility. Facility managers may consequently be provided with a unique and comprehensive look at the equipment being used for all waste generated. Embodiments may thus provide a comprehensive review and analysis of all waste materials generated in a facility.

Program code executed in accordance with embodiments of the invention may highlight any discrepancy between an invoice and a contracted price for waste removal, and may initiate the determination of an estimated savings opportunity, as well as of an implementation time line for solutions. Embodiments may furthermore automatically account for local and national codes, minimizing violations and exposure to potential fines.

Embodiments consistent with the invention may provide synergistic benefits by, in part, leveraging and realizing efficiencies across multiple waste streams. Such benefits typically include lower aggregate costs, more efficient billing and waste removal.

Embodiments executing the program code may present data in a format that facilitates analysis. For example, the program code may help skilled people parse and enter data in a consistent, efficient and easily accessible manner. Data entry may further be steered by prompting users for what to look. In this manner, embodiments of the program code may reduce and/or augment the skill required or possessed by a particular technician tasked to enter the data. The computer facilitated processes may thus help ensure that an assessment is accomplished in a relatively short time span. The programmatic routine may further help provide an industry standard that is comprehensive, consistent, compliant and clear.

Benefits from the automated analysis may include predictions of price savings based on market knowledge. To this end, embodiments may identify current practices, and use those identified practices to determine areas of improvement. Areas of determined improvement and prompted solutions may further lead to such improvements as increased regulatory compliance. For instance, embodiments may determine areas of potential risk that aid in preparation for HIPAA, JAHCO and other inspections. Other benefits may include improved employee safety by automatically recommending tools that reduce sharps container related injuries. Other recommendations may promote a reduction of medical waste volumes, as well as an improved community image by enhancing recycling efforts and promoting more environmentally friendly technologies. Facilities may further realize reduced complexities with regard to managing waste stream areas. That is, embodiments may provide guidance towards achieving operational efficiency, reduction in compliance risks and simplified financial reporting.

Aspects of the invention, while capitalizing on analyzing synergistic effects of comprehensive waste management, nonetheless may keep individual waste streams segregated. For instance, solutions presented to users may include safeguards/processes for keeping hazardous wastes segregated from non-hazardous waste. This can save money because once waste becomes contaminated with a hazardous substance, it becomes hazardous, potentially increasing costs for removal. Automated maintenance prompts may help assure proper making of all chemical and other waste stream containers. Other aspects of the invention may include automated prompts reminding users of chemicals with limited shelf life to use up old stock before ordering or using new stock. Another embodiment may include prompting the efficient and timely ordering of hazardous chemicals.

Automated prompts of some embodiments may guide employee training in hazardous materials management and waste minimization. Such training may include spill prevention and emergency preparedness, including spill cleanup. Program code may additionally determine directions to help facility and waste removal professionals remove such waste efficiently. To realize such benefits, a project manager may oversee the automated analysis to maximize the full economic effect and ensure timely implementation of the complete waste solution.

While the principles of this invention do not limit its forum or application, one desirable embodiment capitalizes on the structure available through the computer networked systems exemplified in FIG. 1. FIG. 1 generally shows a block diagram of a networked computer system 10 configured to facilitate a comprehensive analysis of multiple waste streams for a healthcare facility. The system 10 more particularly comprises one or more client computer(s) 30 coupled to a network 38. Network 38 represents a networked interconnection, including, but not limited to local-area, wide-area, wireless, and public networks (e.g., the Internet). Moreover, any number of computers and other devices may be networked through network 38, e.g., multiple servers. For instance, network 38 may communicate with networked devices located at a state regulatory agency and/or a remote office.

Computer system 10 will hereinafter also be referred to as a "apparatus," "computer," "tool," or "waste stream analysis system," although it should be appreciated that the terms may respectively include many other controller configurations. Moreover, while only one network interface device is shown in FIG. 1, any number of computers and other devices may be networked through network 38. In still another embodiment, the system 10 may be implemented in a stand-alone configuration, i.e., disconnected from another computer or computer network.

Computer 30 typically includes at least one processor 44 coupled to a memory 32. Processor 44 may represent one or more processors (e.g., microprocessors), and memory 32 may represent the random access memory (RAM) devices comprising the main storage of computer 30, as well as any supplemental levels of memory, e.g., cache memories, non-volatile or backup memories (e.g., programmable or flash memories), read-only memories, etc. In addition, memory 32 may be considered to include memory storage physically located elsewhere in computer 30, e.g., any cache memory present in processor 44, as well as any storage capacity used as a virtual memory, e.g., as stored within a database 37, or on another computer coupled to computer 30 via network 38. For instance, exemplary database 37 may include waste stream compliance information 48, as well as pricing information 49 associated with multiple waste streams. Exemplary pricing information may include products and services associated with each waste stream.

Computer 30 also may receive a number of inputs and outputs for communicating information externally. For interface with a user, computer 30 typically includes one or more input devices 33 (e.g., a keyboard, a mouse, a trackball, a joystick, a touch pad, iris/fingerprint scanner, and/or a microphone, among others). The computer 30 additionally includes a display 39 (e.g., a CRT monitor, an LCD display panel, and/or a speaker, among others). It should be appreciated, however, that with some implementations of the computer 30, direct user input and output may be unsupported by the computer, and interface with the server computer 30 may be implemented through a computer or workstation networked with the computer 30.

For additional storage, computer 30 may also include one or more mass storage devices 36 configured to store, for instance, the database 37. Exemplary devices 36 can include: a floppy or other removable disk drive, a flash drive, a hard disk drive, a direct access storage device (DASD), an optical drive (e.g., a CD drive, a DVD drive, etc.), and/or a tape drive, among others. Furthermore, computer 30 may include an interface with one or more networks (e.g., a LAN, a WAN, a wireless network, and/or the Internet, among others) to permit the communication of information with other computers coupled to the network 38. It should be appreciated that computer 30 typically includes suitable analog and/or digital interfaces between processor 44 and each of components 32, 33, 36, 38 and 39.

Computer 30 operates under the control of an operating system 40, and executes various computer software applications, components, programs, modules, e.g., a multi-stream analysis program 45, compliance program 46 and multi-stream pricing program 47, among others. Various applications, components, programs, markers, modules, etc. may also execute on one or more processors in another computer coupled to computer 30 via a network 38, e.g., in a distributed or client-server computing environment, whereby the processing required to implement the functions of a computer program may be allocated to multiple computers over a network.

In general, the routines executed to implement the embodiments of the invention, whether implemented as part of an operating system or a specific application, component, program, engine, process, programmatic tool, object, module or sequence of instructions, or even a subset thereof, may be referred to herein as "computer program code," or simply "program code." Program code typically comprises one or more instructions that are resident at various times in various memory and storage devices in a computer, and that, when read and executed by one or more processors in a computer, cause that computer to perform the steps necessary to execute steps or elements embodying the various aspects of the invention. One of skill in the art should appreciate that embodiments consistent with the principles of the present invention may nonetheless use program code resident at only one, or any number of locations.

Moreover, while the invention has and hereinafter will be described in the context of fully functioning computers and computer systems, those skilled in the art will appreciate that the various embodiments of the invention are capable of being distributed as a program product in a variety of forms, and that the invention applies equally regardless of the particular type of computer readable, signal bearing media used to actually carry out the distribution. Examples of signal bearing, computer readable media include, but are not limited to tangible, recordable type media such as volatile and non-volatile memory devices, floppy and other removable disks, hard disk drives, magnetic tape, optical disks (e.g., CD-ROMs, DVDs, etc.), among others, and transmission type media such as digital and analog communication links.

In addition, various program code described hereinafter may be identified based upon the application or engine within which it is implemented in a specific embodiment of the invention. However, it should be appreciated that any particular program nomenclature that follows is used merely for convenience, and thus the invention should not be limited to use solely in any specific application or engine identified and/or implied by such nomenclature.

Furthermore, given the typically endless number of manners in which computer programs may be organized into routines, procedures, methods, modules, objects, and the like, as well as the various manners in which program functionality may be allocated among various software layers that are resident within a typical computer (e.g., operating systems, libraries, API's, applications, applets, etc.), it should be appreciated that the invention is not limited to the specific organization and allocation of program functionality described herein.

The various software components and resources illustrated in FIG. 1 may be implemented in a number of manners, including using various computer software applications, routines, components, programs, objects, modules, data structures and programs. Those skilled in the art will further recognize that the exemplary environments illustrated in FIG. 1 are not intended to limit the present invention. Indeed, those skilled in the art will recognize that other alternative hardware and/or software environments may be used without departing from the scope of the invention.

FIG. 2 is a flowchart 50 having steps suitable for conducting a comprehensive assessment of multiple waste streams. The flowchart 50 more particularly includes processes used by the system 10 of FIG. 1 to input and analyze waste stream information towards determining pertinent pricing information and implementing a comprehensive plan.

Turning more particularly to the flowchart 50, waste stream data may be collected at block 52. For instance, an onsite technician may conduct a full examination of all waste streams generated by the facility. The individual waste streams may be analyzed from their respective points of generation and collection, through the facility to the staging and storage areas where services are received. This analysis may include examining the methods for transporting the various waste streams through the facility, as well as the number of personnel dedicated to handling the waste. Equipment that includes compactors, bailors, shredders, onsite treatment equipment and other capital equipment related to waste handling may also be examined. Loading docks may be examined, and current waste handling equipment and service levels may be assessed. Interviews may be conducted with key facility personnel. High volume storage areas may also be evaluated.

In one embodiment, the waste stream data may be entered into the system 10 at block 54 of FIG. 2. For instance, a technician(s) may type the results of a waste stream investigation into a handheld or other computer 30. The waste stream data may be stored within the database 37 or other memory. An exemplary database 37 may store pricing information and other waste stream data associated with a plurality of waste streams. As such, the pricing information may include products and services associated with each waste stream.

Because the computer 30 may prompt and guide the gathering and input of the waste data, the user entering the data may not be required to possess the same level of experience and know-how of an analyst not having the benefit of the embodiment's automated processes. Furthermore, an experienced user may benefit from greater efficiency in analyzing data, including access to calculation programs, previously stored examples, compliance figures and/or other stored data.

A user may review at block 56 the assessment results output from the system 10. As discussed herein, the assessment results may include pricing information for a product or service associated with one of the waste streams. As such, pricing information relating to the waste stream data may be determined at block 56 by an analyst, or automatically by the system 30. Examples of pricing information may include haul rates and per ton pricing for solid waste, permanence/per console pricing for confidential documents, per pound/per contained charges for regular medical waste.

In reviewing the results at block 56 of FIG. 2, the user in one embodiment may initiate the retrieval of requested pricing information from the database 37. The database 37 may store pricing information associated with a plurality of waste products and waste services associated with the waste streams. At least some of such pricing information may have been input at block 54.

At block 58, the system 10 may automatically generate a report based on the results. For example, the computer 30 may format and output a paper and/or an electronic copy displaying pricing information to the user. The report may include current cost information for containers and waste streams, projected cost savings, recommended plans to improve operations, etc. Such recommendations may be manually determined using the automatically generated pricing information. Alternatively, an embodiment may automatically generate recommendations by, for instance, matching user input and/or pricing information to known recommendations associated with such data and stored within a database 37. The report may be automatically formatted into a slide type or multimedia presentation, where desired.

Users may implement the recommendations of the results based on the pricing information at block 60 of FIG. 2. For example, administrative paperwork costs may be reduced by consolidating invoices. Practices for more strict waste stream segregation and government compliance may be recommended. Other recommendations may include providing contractual incentives to waste removal companies, as well as discontinuing unsafe practices and encouraging recycling and other "green initiatives" for environmental and financial considerations. Still other recommendations may include implementing waste management training for staff, and purchasing updated containers, refrigerators and other equipment. Additional and/or alternative recommendations may regard developing more efficient waste removal routes, among other practices and equipment improvements.

FIG. 3 is a flowchart 70 having process steps executable by the system of FIG. 1 for assessing and outputting pricing information pertinent to multiple waste streams for the healthcare facility. As such, the processes described in the flowchart 70 may have application in within blocks 54, 56 and 58 of FIG. 2.

Turning more particularly to block 72 of FIG. 3, the computer 30 may prompt user input. For instance, the computer 30 may display a screen having data entry fields soliciting, in one example, the number of containers in a particular department and location of a hospital. The screen may prompt the user to gather and input the times and locations at which the containers are serviced, as well as any information pertaining to the condition of the containers. Other prompts may regard contractual and invoice data particular to the containers. The system 10 may receive and store and the user input at blocks 74 and 76, respectively. As discussed herein, the input may be stored within the database 37.

Compliance information may be retrieved at block 78 of FIG. 3. Exemplary compliance information may account for state and federal regulations, e.g., HIPAA and JAHCO standards. The compliance data may be automatically retrieved in response to the user input or may be initiated in response to a user query. While the compliance data may be stored locally in memory, other compliance data may be retrieved remotely. By augmenting the pricing information with compliance data, the system 10 may account for additional costing data in assessing the potential cost assessment for a facility.

At block 80 of FIG. 3, the computer 30 may initiate the display of pricing information to the user. That is, the computer 30 may present in a retrievable format pricing information relating to multiple waste streams. As such, a user may retrieve pricing information that includes, for example, waste disposal rates and per ton pricing.

For any assessment that the system 10 is not configured to automatically retrieve or otherwise determine based on the pricing information, the computer 30 may receive such an assessment from a user at block 82. For instance, an analyst may review the displayed pricing information at block 80, then input an assessment at block 82. Assessments typically include recommendations for improving existing waste management procedures.

The assessments may be stored at block 84, and where desired, the system 10 may generate a report communicating the pricing information and other assessments at block 86.

Figure 4:
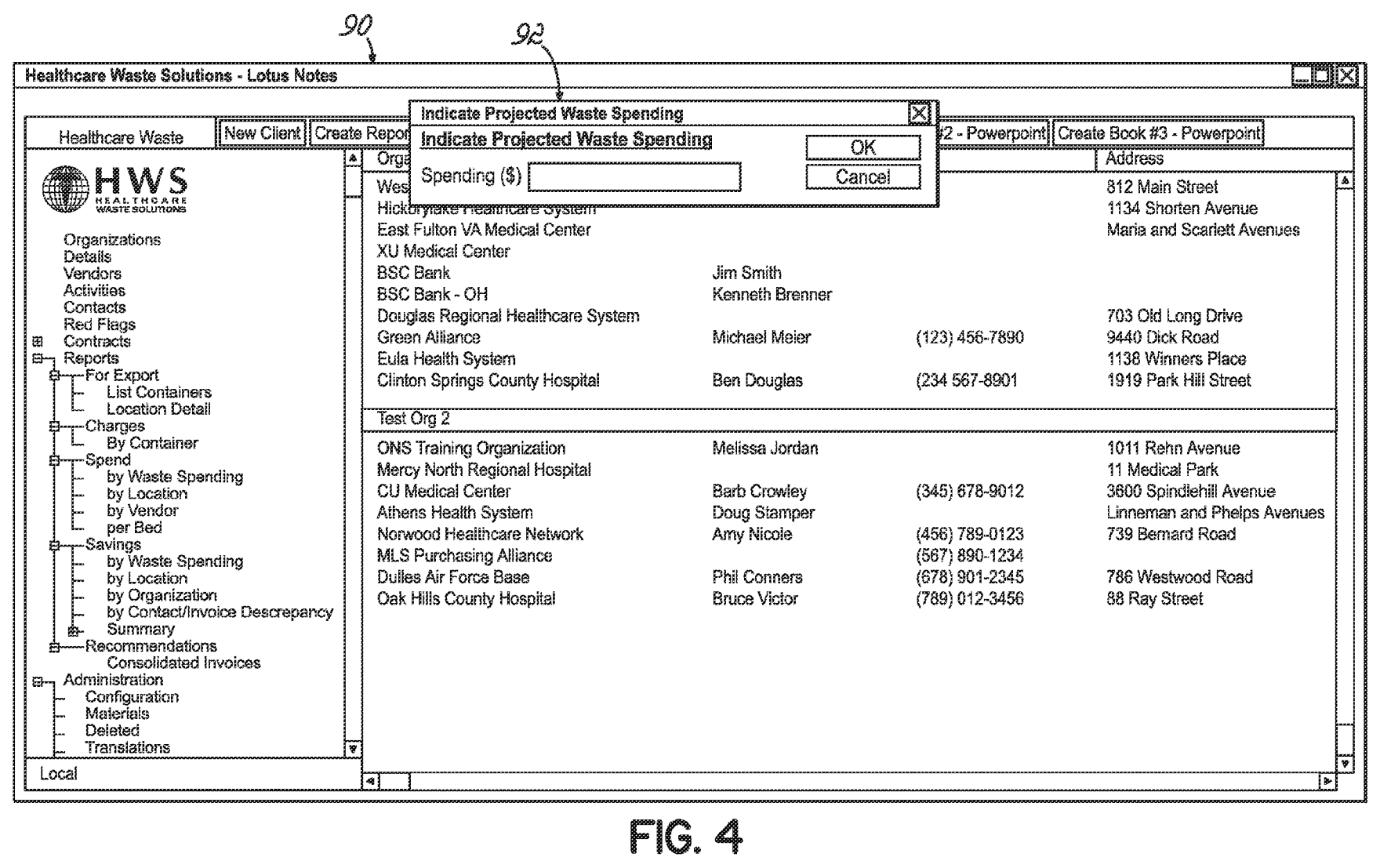

FIG. 4 shows an exemplary computer screen 90 displayed by the system 10 of FIG. 1, and configured to prompt input from the user regarding current waste stream practices. As shown in FIG. 4, a user in prompted to enter a projected waste assessment into a popup field 92. The computer screen 90 may be indicative of the type of display presented to a user at block 72 of FIG. 3.

FIG. 5 shows an exemplary report 100 generated by the system of FIG. 1. The report is efficiently configured to communicate multi-waste stream pricing information to a user in a manner that facilitates its analysis and processing into a solution. As such, the displayed computer screen may be indicative of the type of report generated at block 86 of FIG. 3. The report 100 shows expected savings 102 per waste stream, as may be obtained, for instance, from a recommendation directed to leveraging strong vendor relationships and consolidating services.

FIG. 6 shows an exemplary report 110 generated by the system of FIG. 1 and configured to communicate realized, actual benefits of an implemented waste solution. As such, the report shows pricing information that highlights the benefits of implemented waste solutions by comparing actual, achieved savings 112 achieved by the recommendations to costs incurred prior to their implementation.

While the present invention has been illustrated by a description of various embodiments and while these embodiments have been described in considerable detail, it is not the intention of the applicants to restrict, or in any way limit, the scope of the appended claims to such detail. As such, additional advantages and modifications will readily appear to those skilled in the art. For instance, an embodiment consistent with the invention may automatically generate an assessment by correlating input waste stream information with a stored assessment. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A computer implemented method of assessing medical waste processes, the method comprising:
   receiving user input including waste stream investigation data collected at points of generation and collection for a plurality of waste streams, wherein the waste stream investigation data includes time and location data associated with current waste disposal practices for a plurality of containers;
   receiving user input including contractual and invoice data associated with the current waste disposal practices for the plurality of waste streams and particular to the plurality of containers;
   storing the received waste stream investigation data and contractual and invoice data in a database, wherein the database is resident in a computer of the type including at least one hardware-implemented processor;
   receiving user input from a user to obtain requested pricing information for products or services associated with the plurality of waste streams;
   retrieving the requested pricing information by accessing the database, wherein the database stores pricing information associated with a plurality of waste products and waste services associated with the plurality of waste streams;
   outputting the requested pricing information to the user: and
   Using the hardware-implemented processor, accessing waste stream investigation data and contractual and invoice data stored in the database and generating therefrom, by the processor, a report including at least one operational improvement recommendation and a projected cost savings associated therewith.

2. The computer implemented method of claim 1, wherein the report includes a listing of multiple containers being used at a facility.

3. The computer implemented method of claim 1, wherein the report includes a waste recommendation that includes generating an invoice accounting for at least two of the plurality of waste streams.

4. The computer implemented method of claim 1, wherein the report includes a waste recommendation to improve the medical waste process.

5. The computer implemented method of claim 4, wherein the pricing information includes a comparison between operating costs with the waste recommendation and operating costs without.

6. The computer implemented method of claim 1, wherein retrieving the requested pricing information further comprises retrieving compliance data pertinent to the one of the plurality of waste streams.

7. The computer implemented method of claim 1, further comprising using the requested pricing information to determine a waste recommendation.

8. A computer implemented method of assessing medical waste processes, the method comprising:
   determining pricing information for a plurality of waste streams, including determining waste stream investigation data collected at points of generation and collection for a plurality of waste streams and determining contractual and invoice data associated with the current waste disposal practices for the plurality of waste streams and particular to the plurality of containers, wherein the waste stream investigation data includes time and location data associated with current waste disposal practices for a plurality of containers;
   storing the pricing information within a database configured to store pricing information associated with a plurality of waste products and waste services associated with the plurality of waste streams, wherein the database is resident in a computer of the type including at least one hardware-implemented processor;
   presenting the pricing information in a manner that facilitates waste cost analysis; and
   Using the hardware-implemented processor, accessing the waste stream investigation data and contractual and invoice data stored in the database and generating therefrom, by the processor, a report including at least one operational improvement recommendation and a projected cost savings associated therewith.

9. The computer implemented method of claim 8, further comprising determining a waste recommendation using the pricing information.

10. The computer implemented method of claim 8, wherein determining the waste recommendation further includes automatically determining the waste recommendation by retrieving from a memory the waste recommendation subsequent to receiving the pricing information.

11. The computer implemented method of claim 8, wherein prompting the user to input the pricing information further comprises prompting the user to input data relating to a contract, an invoice and a discrepancy between the contract and the invoice.

12. An apparatus, comprising:
   a processor;
   a memory accessible to the processor, the memory including a database storing pricing information associated with a plurality of waste products and waste services associated with a plurality of waste streams; and
   program code executable by the processor and configured to initiate receiving user input including waste stream investigation data collected at points of generation and collection for the plurality of waste streams, wherein the waste stream investigation data includes time and location data associated with current waste disposal practices for a plurality of containers; receiving user input including contractual and invoice data associated with the current waste disposal practices for the plurality of waste streams and particular to the plurality of containers; storing the received waste stream investigation data and contractual and invoice data in the database; receiving user input from a user to obtain requested pricing information for products or services associated with the plurality of waste streams, retrieving the requested pricing information by accessing the database; outputting the requested pricing information to the user; and accessing waste stream investigation data and contractual and invoice data stored in the database and generating therefrom a report including at least one operational improvement recommendation and a projected cost savings associated therewith.

13. The apparatus of claim 12, wherein the plurality of waste streams include at one waste stream selected from a group consisting of: solid, regulated medical, recycling, confidential document destruction, hazardous and construction debris waste streams.

14. The apparatus of claim 12, wherein the program code is further configured to initiate determining a waste recommendation based on the pricing information by retrieving the waste recommendation from the memory.

15. A program product, comprising:

program code configured to initiate receiving user input including waste stream investigation data collected at points of generation and collection for the plurality of waste streams, wherein the waste stream investigation data includes time and location data associated with current waste disposal practices for a plurality of containers; receiving user input including contractual and invoice data associated with the current waste disposal practices for the plurality of waste streams and particular to the plurality of containers; storing the received waste stream investigation data and contractual and invoice data in a database; receiving user input from a user to obtain requested pricing information for products or services associated with a plurality of waste streams, retrieving the requested pricing information by accessing a database storing pricing information associated with a plurality of waste products and waste services associated with the plurality of waste streams; outputting the requested pricing information to the user; and accessing waste stream investigation data and contractual and invoice data stored in the database and generating therefrom a report including at least one operational improvement recommendation and a projected cost savings associated therewith; and a recordable computer readable medium bearing the program code.

16. The computer implemented method of claim 8, wherein prompting the user to input the pricing information further comprises prompting the user to input data relating to an invoice.

17. The computer implemented method of claim 8, wherein prompting the user to input the pricing information further comprises prompting the user to input data relating to a discrepancy between a contract and an invoice.

* * * * *